United States Patent [19]
Liebert et al.

[11] Patent Number: 6,080,796
[45] Date of Patent: Jun. 27, 2000

[54] DISSOLVING INSECTICIDE IN MONOMER

[75] Inventors: Rebecca B. Liebert, Cranberry Township; Christine B. Hetzer, Monaca, both of Pa.

[73] Assignee: Nova Chemicals Inc., Monaca, Pa.

[21] Appl. No.: 09/136,220

[22] Filed: Aug. 19, 1998

[51] Int. Cl.$^7$ ........................................ C08J 9/28
[52] U.S. Cl. ................ 521/64; 424/405; 521/61; 521/62; 521/63; 521/82; 521/94; 521/95; 521/97; 521/98; 521/146; 521/149
[58] Field of Search ............... 424/405; 521/61, 521/62, 63, 64, 82, 94, 95, 97, 98, 146, 149

[56] References Cited

U.S. PATENT DOCUMENTS

| | | |
|---|---|---|
| 3,658,946 | 4/1972 | Bronstert et al. . |
| 3,660,535 | 5/1972 | Finch et al. . |
| 3,903,202 | 9/1975 | Carter et al. . |
| 5,194,323 | 3/1993 | Savoy . |
| 5,270,108 | 12/1993 | Savoy . |
| 5,704,172 | 1/1998 | Gougeon et al. . |

FOREIGN PATENT DOCUMENTS

| | | |
|---|---|---|
| 2698632 | 6/1994 | France . |

OTHER PUBLICATIONS

Abstract of JP 10036549, date Feb. 10, 1998, Inventor: Y. Toyamaga Source: JPN. Kokai Tokkyo Kaho, 7 pp.

Abstract of FR 2698632, date Jun. 3, 1994, Inventor: J. Jean Source: Fr. Demande, 13 pp.

Abstract of JP 87–88416, date Oct. 20, 1988, Inventor: T. Imakita and Y. Tanaka. Source: JPN. Kokai Tokkyo Kaho, 5 pp.

Abstract of JP 63264670, date Nov. 1, 1988, Inventor: H. Mari and M. Mori, Source: JPN. Kokai Tokkyo Kaho, 2 pp.

Abstract of JP 63159451, date Jul. 2, 1988, Inventor: T. Ikeda and Y. Betppa. Source: Jpn. Kokai Tokkyo Koho, 6 pp.

*Primary Examiner*—John M. Cooney, Jr.
*Attorney, Agent, or Firm*—Kenneth H. Johnson

[57] ABSTRACT

Insecticides, and particularly termiticides, may be dissolved in monomers polymerized to form foamable polymers, such as polystyrene. The resulting monomer and insecticide may then be polymerized in a conventional manner and either impregnated with a blowing agent or expanded using an extrusion process to produce polymeric foam having insecticidal properties. The polymer may also contain a flame retardant. Such polymers and the foam made therefrom may be used in the construction industry, particularly where insect infestation is a concern.

7 Claims, No Drawings

DISSOLVING INSECTICIDE IN MONOMER

FIELD OF THE INVENTION

The present invention relates to polymers of vinyl aromatic monomers which contain insecticides. More particularly, the present invention relates to foamable or expandable polymers of vinyl aromatic monomers which contain insecticides.

BACKGROUND OF THE INVENTION

Polymeric foam is finding increasing application in the construction industry. However, under some conditions the foam may be subject to insect infestation, and particularly termite infestation. There is a need for methods of rendering polymeric foams resistant to insects.

U.S. Pat. No. 5,194,323 issued Mar. 16, 1993 and U.S. Pat. No. 5,270,108 issued Dec. 14, 1993, both assigned to AFM Corporation, disclose and claim polymeric foams suitable for construction purposes which have been treated with a borate compound to inhibit insect and particularly termite infestation. The patent does not teach or suggest that the insecticide could be added to the monomer prior to polymerization.

U.S. Pat. No. 5,704,172 issued Jan. 6, 1998, assigned to The Dow Chemical Company, teaches a rigid polymer foam having a plurality of grooves crossing in diagonal configuration which facilitates the application of insecticides to such rigid foam. The foam may be used for construction purposes. The patent teaches an external post fabrication application of insecticide and does not suggest adding the insecticide to the monomer prior to polymerization.

Chemical Abstracts of Japanese Kokai 10036549 A2 published Feb. 10, 1998, and Japanese Kokai 63254143 published Oct. 20, 1988 teach applying anti-termite agents to the exterior of foams. The abstracts do not teach or suggest incorporating the insecticides into a monomer used to prepare the polymer.

The Chemical Abstract of French Patent 2698632 published Jun. 3, 1994 teaches the production of very light weight foams, preferably polyurethanes having a density from 5 to 20 g/l. While the patent teaches polyurethanes are preferred it also teaches that the foam may comprise polystyrene, polyacrylates, and polycarbonates. The disclosure suggests the active substances are preferably introduced into the mixture before polymerization. However, examples 1 and 4 of the patent illustrate the invention using polystyrene foam. The active ingredient is not introduced into the monomer but rather is introduced into "a viscous but liquid styrene prepolymer which has been prepared by heating at 60° C. for an unspecified period of time a mixture of 1000 g of styrene monomer, 1 g of benzoyl peroxide and 70 g of tributyl phosphate as a plastifier". MALATHION is added to the resulting prepolymer. The temperature is adjusted to 45° C. and the mixture is stirred while nitrogen is bubbled through the mixture to obtain a foam having a specific weight of 12 g/l. On a fair reading of the patent disclosure in its entirety one would not conclude that the active ingredient is added to the styrene monomer but rather is added to a partially polymerized polymer. This teaches away from the subject matter of the present invention.

Chemical Abstracts of Japanese Kokai 63264670 A2 published Nov. 1, 1988 and Japanese Kokai 63159451 A2 published Jul. 2, 1988 teach impregnating polystyrene beads with boron compounds or with compounds selected from the group consisting of Phoixom, Fenitrothion, Cyanophos, Acephate and Prothiophos, respectively. The patents do not teach dissolving the active ingredient in the monomer prior to polymerization.

None of the above art discloses dissolving the insecticide in the monomer prior to polymerization.

SUMMARY OF THE INVENTION

Accordingly, one aspect of the present invention provides a process for incorporating an insecticide into a thermoplastic polymer comprising dissolving from 100 to 10,000 ppm of said insecticide into one or more monomers which are polymerized to form said thermoplastic polymer and polymerizing said one or more monomers.

The present invention further provides a termite resistant fire retardant foamable and foamed polymer containing such insecticides.

BEST MODE

The thermoplastic of the present invention may comprise from 100 to 60 weight %, preferably from 100 to 80 weight % of one or more $C_{8-12}$ vinyl aromatic monomers and up to 40 weight %, preferably not more than 20 weight %, of other ethylenically unsaturated copolymerizable monomers. Examples of suitable vinyl aromatic monomers include, but are not limited to, styrene, alpha-methyl styrene, aromatic $C_{1-4}$ alkyl substituted styrenes such as p-methyl styrene, p-ethyl styrene, p-isopropyl styrene, p-tert-butyl styrene and the like. Other ethylenically unsaturated copolymerizable monomers may also be used, including, for example, acrylic acid, methacrylic acid, maleic anhydride, methyl methacrylate, ethyl acrylate, methyl acrylate, butyl acrylate, acrylonitrile, methacrylonitrile and the like.

A particularly useful thermoplastic is polystyrene in which the monomer is 100% styrene.

The insecticide may be dissolved in one or more of the monomers, preferably the vinyl aromatic monomer, most preferably styrene, used to prepare the thermoplastic in accordance with the present invention in an amount from 100 to 10,000 parts per million (ppm) (corresponding to from 0.01 to 1 weight %) preferably from 300 to 5,000 ppm (corresponding to from 0.03 to 0.5 weight %) based on the total weight of the monomer(s). In the case where the thermoplastic is a homopolymer the amount of insecticide in the monomer should correspond to the amount of insecticide in the polymer. If the thermoplastic is a copolymer, then the amount of insecticide in the monomer should be selected so that the amount of insecticide in the resulting polymer is in the range from 300 to 5,000 ppm based on the weight of the polymer.

While a number of insecticides are available some useful insecticides may be selected from the group consisting of 1-[(6-chloro-3-pyridinyl)methyl]-4,5-dihydro-N-nirto-1H-imidazol-2-amine and 3-(2,2-dichloroethenyl)-2,2-dimethylcyclopropanecarboxylic acid cyano(3-phenoxyphenyl)-methyl ester (cypermethrin), the active ingredient in, for example, Demon TC sold by Zeneca; 3-(2,2-dichloroethenyl)-2,2-dimethylcyclopropanecarboxylic acid (3-phenoxyphenyl) methyl ester (permethrin), the active ingredient in, for example, Dragnet FT and Torpedo sold by Zeneca; and 1-[(6-chloro-3-pyridinyl)methyl]-4,5-dihydro-N-nirto-1H-imidazol-2-amine (imidacloprid), the active ingredient in, for example, Premise sold by Bayer.

The thermoplastic of the present invention may be polymerized in any conventional manner. Generally thermoplastics comprising a major amount of a vinyl aromatic monomer and a minor amount of one or more copolymerizable monomers may be polymerized using a thermal and/or free radical initiation. The process may be a bulk polymerization in which the monomers and, optionally, a minor amount of a diluent such as ethyl benzene, forms the reaction medium. The process may be a suspension or emulsion process in which the monomer(s) is/are suspended or dispersed in a different, non-hydrocarbon, typically aqueous phase and the polymerization takes place in the dispersed monomer droplets (e.g. suspension) or in a micelle into which monomer diffuses from the monomer droplets (e.g. emulsion).

According to one aspect of the present invention in which the polymer is prepared in a suspension or emulsion, the monomers are suspended in water, from about 50 to 500 parts (preferably, about 75 to 250 parts) by weight, per 100 parts by weight of the monomers using an effective amount of one or more suitable suspending agents. Any of the suspending agents useful in the suspension polymerization of vinyl aromatic polymers may be used. Examples of suitable suspending agents include finely divided water-insoluble inorganic substances such as tricalcium phosphate and the like as well as water-soluble polymers such as polyvinyl alcohol, alkyl aryl sulfonates, hydroxyethyl cellulose, polyacrylic acid, methyl cellulose, polyvinyl pyrrolidone, and low molecular weight (preferably having an Ms less than about 5,000) polyalkylene glycols (e.g. polyethylene glycols and polypropylene glycols) and the like. Auxiliary suspending agents such as sodium linear alkylbenzene sulfonates may also be employed. The use of tricalcium phosphate together with a sodium linear alkylbenzene sulfonate is particularly useful. The amount of the suspending agent necessary will vary depending on a number of factors but will generally be from about 0.01 to 1 part by weight per 100 parts by weight of the vinyl aromatic polymer. One or more surfactants such as a polyoxyalkylene derivative of sorbitan monolaurate or other fatty acid ester, an ethylene oxide/propylene oxide block copolymer, or other non-ionic or anionic surface active agent can be added to the aqueous suspension if desired. The preferred amount of surfactant is from about 0.01 to 1 part by weight per 100 parts by weight of monomer.

In addition to the monomers, the aqueous suspension may further include a free radical initiator or free radical initiator system. The free radical generator may be a peroxide such as hydrogen peroxide or benzoyl peroxide, or a persulfate initiator.

The reaction mixture is heated to initiate polymerization, either thermally or by a free radical catalyst. After the monomers are polymerized to form particles or beads (generally resulting from the suspension process) or microparticles (generally resulting from the emulsion process), they may be separated from the aqueous phase and washed. The thermoplastic polymer beads are typically from about 0.1 to 2 mm in average diameter.

Generally, the polymer bead is impregnated with a blowing agent to make expandable thermoplastic beads (polystyrene). Typically the beads may be impregnated with from 1 to 10 weight %, preferably from about 3 to 8 weight %, based on the weight of the polymer of one or more blowing agents selected from the group consisting of $C_{4-6}$ alkanes. Typical blowing agents include butane, pentane and hexane. While the CFC's and HCFC's such as dichlorodifluoromethane, trichlorofluoromethane and dichlorofluoromethane have some suitable properties as blowing agents their use is not recommended.

In the suspension process the polymer beads may be impregnated either concurrently with the later part of the polymerization or after polymerization.

The resulting beads are stored, preferably, in a cool dark environment. When used to produce a foam product, typically the beads are first partially expanded and then placed in a mold and fully expanded resulting in a fusion of the foamed beads and a closed cell foam. Generally for construction industry purposes the foam will take the form of a sheet.

In bulk polymerization, the monomer(s), as described above, comprising one or more vinyl aromatic monomers and copolymerizable monomers, are fed to one or more reactors in a chain or series of reactors at increasing temperatures up to about 230° C. in which the monomers are polymerized to increasing conversion of at least about 65% conversion. The polymer leaves the last reactor in the chain, in the case of a tower process as illustrated by U.S. Pat. No. 3,658,946, issued Apr. 25, 1972, assigned to BASF and U.S. Pat. No. 3,660,535, issued May 2, 1972, assigned to The Dow Chemical Company, or the last horizontal reactor in the chain, in the case of a Monsanto type process as illustrated by U.S. Pat. No. 3,903,202, issued Sep. 2, 1975, assigned to Monsanto, and travels through a preheater. The preheater heats the polymer melt to a temperature of from about 200° C. to 270° C. to increase the vapor pressure of the volatiles and reduce the viscosity of the melt to permit it to foam. The polymer melt is then passed typically through a zone of lowered pressure such as a falling strand devolatilizer or an extruder having vacuum ports to remove unreacted monomer and solvent (ethylbenzene) from the polymer. The polymer is then typically extruded as strands, cooled, generally in a water bath, and chopped into pellets.

The resulting pellets may be foamed concurrently with extrusion. The pellets are passed through an extruder or back to back extruders. Initially the pellets are subjected to heat and shear to form a molten plastic mass. Towards the end of the process a foaming agent under pressure is injected into the molten thermoplastic mass. Typically this occurs in the extruder in a zone having mixing pins rather than the flights of a screw. The foaming agent may be one of those listed above or it may be an atmospheric gas such as carbon dioxide or nitrogen. The thermoplastic mass is maintained under pressure so that it will not significantly foam prior to extrusion. The thermoplastic is then extruded either as a sheet or as a cylinder which is then slit and opened into a sheet. The resulting sheet is suitable for a number of applications including foam insulation in the construction industry.

In a preferred embodiment of the present invention, the polymer may further incorporate a flame retardant. Typically the flame retardant is incorporated into the polymer in an amount from 5,000 ppm to 50,000 ppm (0.5 weight % to 5.0 weight %), preferably from 7,500 ppm to 15,000 ppm. In the suspension or emulsion process, the flame retardant may be added to the monomer or aqueous phase, depending on solubility in the monomer/polymer. In the bulk process and optionally in the suspension and emulsion process, the flame retardant may be added to the resulting polymer by coating it or adding it as part of an additive package in an extrusion process. Suitable flame retardants are known to those skilled in the art. Some flame retardants include hexabromocyclododecane, dibromoethyldibromocyclohexane, tetrabromocyclooctane, tribromophenol alkyl ether, tetrabromobisphenol A-bis(2,3-dibromopropyl ether).

The present invention will now be illustrated by the following examples. In the examples, unless other wise indicated, parts means parts by weight (e.g. grams) and percent means weight percent.

EXAMPLE 1

Cypermethrin was dissolved in styrene monomer at a level of 0.3 weight %. The styrene monomer was suspended in an aqueous phase in the presence of 0.20 weight % of a primary inorganic suspending agent and 0.25 weight % of a secondary anionic surfactant suspending agent, based on the weight of the styrene monomer. Low and high temperature peroxide initiators were added at levels of 0.34 and 0.066 weight %, respectively. Nucleation agents were also added at levels of 0.2 weight %. The resulting suspension was heated to 90° C. The first phase of the polymerization of styrene monomer to polymer was carried out at 90° C. over 5.5 hours. The suspension is then heated to 130° C. The second phase of the polymerization was carried out at 130° C. over 2 hours. The resulting beads were washed, dried and re-suspended in water with additional primary suspension agent. The suspension was heated from 70–115° C. over 2.5 hours as 7.2 weight % of pentane was added to the system. The system was held at 115° C. for 1.5 hours to fully impregnate the polystyrene beads. The resulting beads were then washed, dried and lubed with 0.15 weight % stearate.

The resulting beads were then partially expanded in steam. After aging, the pre-expanded beads were placed in a closed mold and heated to 115° C. to fully expand and fuse them together. The result is a sheet or shape of foam. No negative performance characteristics were observed in the blowing of the foam.

What is claimed is:

1. A process for preparing an expandable bead of a thermoplastic polymer using a the suspension polymerization of a monomer mixture consisting of 100 to 60 weight % of one or more monomers selected from the group consisting of styrene, alpha-methyl styrene and p-methyl styrene and from 0 to 40 weight % of a monomer selected from the group consisting of acrylic acid, methacrylic acid, maleic anhydride, methyl methacrylate, methyl acrylate and ethyl acrylate, and impregnating said bead with from 1 to 10 weight % based on the weight of said thermoplastic of one or more blowing agents selected from the group consisting of butane, pentane and hexane wherein there is added to one or more of said monomers prior to polymerization from 100 to 10,000 ppm based on the total weight of monomers of an insecticide selected from the group consisting of 1-[(6-chloro-3-pyridinyl)methyl]-4,5-dihydro-N-nitro-1H-imidazol-2-amine; 3-(2,2-dichloroethenyl)-2,2-dimethylcyclopropanecarboxylic acid cyano(3-phenoxyphenyl)-methyl ester; and 3-(2,2-dichloroethenyl)-2,2-dimethylcyclopropanecarboxylic acid (3-phenoxyphenyl)methyl ester.

2. The process according to claim 1, wherein said one or more monomers mixture is 100 weight % of styrene.

3. The process according to claim 2, wherein said insecticide is incorporated into said thermoplastic in an amount form 300 to 5,000 ppm based on the total weight of the monomers.

4. The process according to claim 3, further comprising adding to said monomers from 5,000 to 30,000 ppm based on the weight of said monomers of a flame retardant selected from the group consisting of hexabromocyclododecane, dibromoethyldibromocyclohexane, tetrabromocyclooctane, tribromophenol allyl ether, tetrabromobisphenol A-bis(2,3-dibromopropyl ether).

5. The process according to claim 4, wherein said insecticide is 1-[(6-chloro-3-pyridinyl)methyl]-4,5-dihydro-N-nitro-1H-imidazol-2-amine.

6. The process according to claim 4, wherein said insecticide is 3-(2,2-dichloroethenyl)-2,2-dimethylcyclopropanecarboxylic acid cyano(3-phenoxyphenyl)-methyl ester.

7. The process according to claim 4, wherein said insecticide is 3-(2,2dichloroethenyl)-2,2-dimethylcyclopropanecarboxylic acid (3-phenoxyphenyl) methyl ester.

* * * * *